United States Patent
Koh et al.

(10) Patent No.: US 7,968,204 B2
(45) Date of Patent: Jun. 28, 2011

(54) ABRASION-RESISTANT OPTICAL ARTICLE AND PROCESS FOR MANUFACTURING THEREOF

(75) Inventors: Michelle Kim Cheng Koh, Charenton-le-Pont (FR); Xiao Feng Luo, Charenton-le-Pont (FR); Zheng Wang, Chareton-le-Pont (FR)

(73) Assignee: Essilor International (Compagnie Generale d'Optique), Charenton Le Pont (FR)

( * ) Notice: Subject to any disclaimer, the term of this patent is extended or adjusted under 35 U.S.C. 154(b) by 65 days.

(21) Appl. No.: 12/501,640

(22) Filed: Jul. 13, 2009

(65) Prior Publication Data
US 2010/0016463 A1 Jan. 21, 2010

(30) Foreign Application Priority Data

Jul. 21, 2008 (EP) .................................... 08305410

(51) Int. Cl.
*C09D 183/08* (2006.01)
*B32B 9/04* (2006.01)
*B32B 19/00* (2006.01)

(52) U.S. Cl. ................ 428/447; 106/286.4; 106/287.13; 106/287.16; 106/287.32; 106/287.34; 428/702

(58) Field of Classification Search ........................ None
See application file for complete search history.

(56) References Cited

U.S. PATENT DOCUMENTS

| 4,889,768 | A | 12/1989 | Yokoshima et al. | |
| 7,576,167 | B2 * | 8/2009 | Mori et al. | 528/13 |
| 2004/0096666 | A1 | 5/2004 | Knox et al. | |

FOREIGN PATENT DOCUMENTS

| EP | 1 156 053 | | 11/2001 |
| JP | 2006-52168 | * | 2/2006 |
| WO | WO 00/27931 | | 5/2000 |
| WO | WO 2005/007751 | * | 1/2005 |

OTHER PUBLICATIONS

"Preparation and Characterization of High Refractive Index Thin Films of TiO2/Epoxy Resin Nanocomposites" authored by Guan et al. and published in the Journal of Applied Polymer Science (2006) 102, 1631-36.*
Abstract for CN 1970565 (2007).*
Abstract for JP 2006-52168.*
translation of paragraph [0034] of JP 2006-52168.*
Nakayama et al., "Synthesis of Novel UV-Curable Difunction Thiourethane Methacrylate and Studies on Organic-Inorganic Nanocomposite Hard Coatings for High Refractive Index Plastic Lenses" Progress in Organic Coatings, 62(3):274-284 (2008).

* cited by examiner

*Primary Examiner* — Marc S Zimmer
(74) *Attorney, Agent, or Firm* — Occhiuti Rohlicek & Tsao LLP

(57) ABSTRACT

An optical article includes a transparent substrate and an abrasion-resistant layer appended to at least one surface of the substrate. The abrasion-resistant layer results from the reaction mixture of:
a first organo-silane chosen from thiocarbamate-silane matrix precursor containing at least one terminal alkoxysilane group, or hydrolysates thereof, the thiocarbamate-silane compound resulting from the reaction of a polythiol including at least two —SH thiol substituent, with an isocyanato-silane compound represented by the general formula:

$(R_1)_3Si-R_2-N=C=O$ wherein $R_1$ represents a group selected from linear or branched $(C_1-C_6)$ alkoxy, and $R_2$ represents a group selected from linear or branched $(C_1-C_6)$ alkylene, linear or branched $(C_1-C_6)$ alkenylene, arylene, and $(C_5-C_{12})$cycloakylene, each of these groups being optionally substituted by one to six groups selected from halogen, alkoxy, carboxy, alkylcarbonyl, alkoxycarbonyl, and perfluoroalkyl,
an inorganic oxide,
a curing catalyst for said thiocarbamate-silane, and
a solvent for said organo-silane.

17 Claims, No Drawings

ABRASION-RESISTANT OPTICAL ARTICLE AND PROCESS FOR MANUFACTURING THEREOF

CROSS-REFERENCE TO RELATED APPLICATIONS

This application claims priority to European Patent Application No. 08305410.6, filed Jul. 21, 2008. The content of which is hereby incorporated by reference in its entirety.

The present invention relates to improved high refractive abrasion-resistant coatings, suitable for mineral or organic glasses. In particular, the present invention relates to inorganic/organic hybrid coating materials produced by a sol-gel process.

The coatings of the present invention have high refractive index, as well as optical abrasion resistance and transparency.

Optical articles made with plastic materials usually suffer from their poor scratch resistance and low hardness. Although plastics are finding wide uses in areas where transparent qualities are necessary, they are not without problems. Plastic lenses, for example, easily get scratched when compared with conventional mineral glass lenses.

Various types of protective coating materials have been used to improve the abrasion resistance and hardness of transparent polymer material surfaces, such as polycarbonate resins. Silicone-based abrasion-resistant coatings have also been developed for plastics used in ophthalmic and non-ophthalmic lens applications. Among silicone coatings are hydrolysates of organo-silane compounds, such as tetraalkoxysilanes, and trialkoxyalkylsilanes, eventually having reactive groups present in the alkyl groups.

For example, U.S. Pat. No. 4,211,823 or EP 0 614 957 describes abrasion-resistant coating compositions containing silica, hydrolyzed epoxy-silanes and aluminum chelates.

These reactants undergo a comparable sol-gel reaction similar to typical metal alkoxide chemistry, thereby producing an insoluble network material containing organic moieties along with silica moieties.

The eye lens industry is focusing on producing high index lenses (refractive index, about 1.6-1.7), which require high refractive index (1.63-1.68) abrasion-resistant coatings. The refractive index of presently available organic abrasion-resistant coatings is about 1.5, making them unsuitable for high index lenses. The large difference between the lens substrate refractive index and the abrasion-resistant coating refractive index causes unsightly fringes. Therefore, there is an immediate need for abrasion-resistant coatings that have high refractive index as well as excellent abrasion resistance.

Two ways of limiting the occurring of fringes, can be used:
- an intermediate refractive index layer, such as described in Patent FR 2 834 345, is placed between the low refractive index of abrasion-resistant coating and the lens substrate, or as an alternative,
- an abrasion-resistant coating with refractive index matching that of the lens substrate is used in lieu of the low refractive index abrasion-resistant coating.

Usual high refractive index abrasion-resistant compositions contain the association of a low refractive index organo-silane matrix (typically about 1.50) and high refractive index inorganic oxide colloids (typically greater than 1.80). The refractive index of the abrasion-resistant coating can be adjusted by varying the proportions of the colloid to matrix.

If the mismatch between the abrasion-resistant coating refractive index and the lens substrate refractive index is large, the first method will be ineffective in some cases. For example fringes may still occur when the mismatch between the intermediate layer refractive index and the abrasion-resistant coating refractive index is too large.

Given the trend of increasingly higher refractive index lens, the second method is therefore more sustainable. There is a need for developing an abrasion-resistant coating with a high refractive index, typically a refractive index higher than 1.50.

There are two critical drawbacks for such an abrasion-resistant coating: (1) the large difference in the refractive indices of the inorganic oxide and organo-silane increases the haze level of the abrasion-resistant coating; and (2) high proportions of inorganic oxides to organo-silane is needed to achieve high refractive index of abrasion-resistant coating, so that poor adhesion of the an abrasion-resistant coating to lens substrate can occur.

The present invention intends to remedy this situation and proposes new coated articles being abrasion-resistant, in which the presence of a new organo-silane compound heightens the refractive index of the articles, without increasing haze. Moreover, the inorganic oxide content can be lowered compared to know abrasion-resistant coatings having the same refractive index.

The present invention uses a sol-gel composition intended for preparing an abrasion-resistant coating that advantageously has a higher refractive than known abrasion-resistant coatings, while keeping in the same time a satisfactory hardness level.

The sol-gel composition according to the invention contains inorganic oxide, and a particular organo-silane compound used as a precursor for the coating. Such a specific organo-silane is used as a matrix precursor that leads to a high refractive index matrix coating after curing.

To obtain a high index matrix, the present inventors have synthesized new organo-silane matrix precursors. Therefore, the organo-silane matrix precursor according to the present invention enables to lower the haze level of the abrasion-resistant coating. Moreover the matrix precursor according to the present invention enables to introduce lower proportions of inorganic oxides to achieve the hardness performances of a high refractive index abrasion-resistant coating, thus reducing the adverse effect caused by high proportion of inorganic oxides.

Furthermore articles coated with an abrasion-resistant composition according to the present invention exhibit optical properties with high quality so that they are particularly suitable for optical lenses and more specifically ophthalmic lenses. Indeed, the application of abrasion-resistant layers on optical substrates as described in the present application allows to get optical lenses with a relative transmission factor in the visible of at least 85% associated to a haze value below 0.2.

By "abrasion-resistant coating" or "hard-coat", in the meaning of the invention, is meant an abrasion-resistant monolayer or an abrasion-resistant bilayer. More details related to this abrasion-resistant coating will be defined in the following description.

By "substrate", in the meaning of the invention, is meant all mineral or organic glasses which may optionally be coated with a tinted coating, with a photochromic coating, with a protective coating (to resist for example to the solvent's degradation), or with an abrasion-resistant coating. It is also understood that the substrate may be all mineral or organic glasses in which the photochromic or tinted function may be included in the material of substrate itself.

An object of the present invention is therefore to provide an optical article, such as an ophthalmic lens, comprising an organic or mineral glass substrate, and at least one abrasion-resistant coating layer wherein the interference fringe phenomenon linked to the refractive index difference of the substrate and the abrasion-resistant coating layer occurring at the interface between the substrate and the layer is significantly mitigated.

Another further object of the invention is to provide a method for manufacturing an optical article such as defined here above.

More precisely, the invention relates to an optical article comprising a transparent substrate, and a high refractive and abrasion-resistant layer coated onto at least one surface of said substrate, wherein said layer results from reacting and curing a mixture containing the following compounds:
a first organo-silane compound chosen from thiocarbamate-silane compounds containing at least one terminal alkoxysilane group, or hydrolysates thereof, said thiocarbamate-silane compound resulting from the reaction of a polythiol comprising at least two —SH thiol substituent, with an isocyanato-silane compound represented by the general formula:

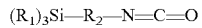

wherein $R_1$ represents a group selected from linear or branched $(C_1\text{-}C_6)$ alkoxy, and $R_2$ represents a group selected from linear or branched $(C_1\text{-}C_6)$ alkylene, linear or branched $(C_1\text{-}C_6)$ alkenylene, arylene, and $(C_5\text{-}C_{12})$ cycloakylene, each of these groups being optionally substituted by one to six groups selected from halogen, alkoxy, carboxy, alkylcarbonyl, alkoxycarbonyl, and perfluoroalkyl, an inorganic oxide selected from the group consisting of iron, titanium, cerium, zirconium, antimony, zinc, tin oxides, silica, and composite oxides thereof,
a curing catalyst for said organo-silane, and
a solvent for said organo-silane.

Such an optical article preferably comprises a high refractive and abrasion-resistant layer that has a refractive index higher than 1.55. The present invention therefore provides with optical articles having a refractive index higher than 1.58, and an abrasion resistance measured according Bayer ASTM F 735-81 between 0.9 and 1.6.

The present invention also relates to a process for manufacturing an optical article comprising the steps of
1) preparing a coating solution by mixing
a first organo-silane chosen from thiocarbamate-silane compounds containing at least one terminal alkoxysilane group, or hydrolysates thereof, said thiocarbamate-silane compound resulting from the reaction of a polythiol comprising at least two —SH thiol substituent, with an isocyanato-silane compound represented by the general formula:

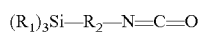

wherein $R_1$ represents a group selected from linear or branched $(C_1\text{-}C_6)$ alkoxy, and $R_2$ represents a group selected from linear or branched $(C_1\text{-}C_6)$ alkylene, linear or branched $(C_1\text{-}C_6)$ alkenylene, arylene, and $(C_5\text{-}C_{12})$ cycloakylene, each of these groups being optionally substituted by one to six groups selected from halogen, alkoxy, carboxy, alkylcarbonyl, alkoxycarbonyl, and perfluoroalkyl,
an inorganic oxide selected from the group consisting of iron, titanium, cerium, zirconium, antimony, zinc, tin oxides, silica, and composite oxides thereof,
a curing catalyst for said organo-silane, and
a solvent for said organo-silane,
2) coating a substrate with said solution, and
3) curing the coating, thereby obtaining a high refractive and abrasion-resistant layer coated onto said substrate.

According to the present invention, a coating solution containing such a thiocarbamate-silane and a low content of inorganic oxide, can lead to a coated substrate that has a refractive index within the range of from 1.55 to 1.66.

Thiocarbamate-silane Matrix Precursor

The abrasion-resistant layer is made of a first organo-silane chosen from thiocarbamate-silane matrix precursor compounds containing at least one terminal alkoxysilane group, or hydrolysates thereof.

Said thiocarbamate-silane matrix precursor is obtained by reacting isocyanato-silane with polythiol. Such a thiocarbamate-silane shows a high refractive index, typically higher than 1.47, and can lead to a matrix with high refractive index, typically to a minimum of 1.55.

The isocyanato-silane compound is represented by the general formula:

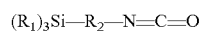

wherein $R_1$ represents a group selected from linear or branched $(C_1\text{-}C_6)$ alkoxy, and $R_2$ represents a group selected from linear or branched $(C_1\text{-}C_6)$ alkylene, linear or branched $(C_1\text{-}C_6)$ alkenylene, arylene, and $(C_5\text{-}C_{12})$ cycloakylene, each of these groups being optionally substituted by one to six groups selected from halogen, alkoxy, carboxy, alkylcarbonyl, alkoxycarbonyl, and perfluoroalkyl.

$R_1$ is preferably selected from methoxy, ethoxy, and propyloxy.

$R_2$ is preferably selected from linear or branched $(C_1\text{-}C_6)$ alkylene, phenylene and cyclopropylene.

For example, isocyanato-silane compounds that may be used in this invention are: 1-trimethoxysilane-4-isocyanato-benzene (CAS Number 956700-82-6), 1-trimethoxysilane-3-isocyanato-benzene (CAS Number 151707-74-3), 1-trimethoxysilane-2-isocyanato-cyclopropane (CAS Number 684278-10-2), 1-trimethoxysilane-3-isocyanato-propane, and 3-(triethoxysilyl)propyl isocyanate (CAS Number 24801-88-5).

By "polythiol" compound is meant an organic compound containing at least two —SH groups.

The polythiol compound should contain at least two —SH thiol substituents, and can contain up to three or four —SH thiol substituents. The polythiol compound preferably has 2 to 30 carbons atoms, more preferably from more preferably from 3 to 6. The polythiol compound preferably has a refractive index which is at least 1.55.

The polythiol compound can be selected from the group consisting of 4-mercaptomethyl-3,6-dithia-1,8-octanedithiol, trimethylolpropane tris(3-mercaptopropionate), pentaerythritol tetrakis(3-mercaptoacetate), trimethylolpropane tris(3-mercaptoacetate), 4-t-butyl-1,2-benzenedithiol, bis-(2-mercaptoethyl)sulfide, 4,4'-thiodibenzenethiol, benzenedithiol, glycol dimercaptoacetate, glycol dimercaptopropionate ethylenebis(3-mercaptopropionate), polyethylene glycol dimercaptoacetates, polyethylene glycol di(3-mercaptopropionates), pentaerythritol tetrakis(3-mercapto-propionate), mercapto-methyl tetrahydrothiophene, tris-(3-mercaptopropyl)isocyanurate, 2-mercaptoethylsulphide, 1,2,3-trimercaptopropane, 2,2-bis(mercaptomethyl)-1,3-propanedithiol, dipentaerythrithiol, 1,2,4-trimercaptomethyl benzene, 2,5-dimercaptomethyl-1,4-dithiane, bisphenofluorene bis(ethoxy-3-mercaptoproprionate), 4,8-bis(mercaptomethyl)-3,6,9-trithia-1,11-undecanedithiol, 2-mercaptomethyl-2-methyl-1,3-propanedithiol, 1,8-dimercapto-3,6-dioxaoctane, thioglycerol bismercapto-acetate, and mixtures thereof.

Examples of preferred polythiol compounds are as follows in Table 1:

TABLE 1

| Chemical Name | CAS | Molecular Structure |
| --- | --- | --- |
| 1,2,3-trimercaptopropane | 4756-13-2 | HS-CH$_2$-CH(SH)-CH$_2$-SH |
| 2,5-dimercaptomethyl-1,4-dithian | 136122-15-1 | HSCH$_2$-(1,4-dithiane)-CH$_2$SH |
| Trimethylolpropane tris(3-mercaptopropionate) | 33007-83-9 | CH$_3$CH$_2$-C(CH$_2$O-C(=O)-CH$_2$CH$_2$SH)$_3$ |
| Pentaerythritol tetrakis(2-mercaptoacetate) | 10193-99-4 | C(CH$_2$O-C(=O)-CH$_2$SH)$_4$ |
| 4,4'-Thiobisbenzenethiol | 19362-77-7 | HS-C$_6$H$_4$-S-C$_6$H$_4$-SH |
| Ethylene glycol bis(mercaptoacetate) | 123-81-9 | HSCH$_2$-C(=O)-OCH$_2$CH$_2$O-C(=O)-CH$_2$SH |
| 2-Mercaptoethyl sulphide | 3570-55-6 | HS-CH$_2$CH$_2$-S-CH$_2$CH$_2$-SH |
| 4-mercaptomethyl-3,6-dithia-1,8-octanedithiol | 131538-00-6 | CH$_2$SH–CH(SCH$_2$CH$_2$SH)–CH$_2$SCH$_2$CH$_2$SH |
| Pentaerythritol tetrakis (3-mercapto-propionate) | 7575-23-7 | C(CH$_2$OC(=O)CH$_2$CH$_2$SH)$_4$ |
| 1,2-Benzenedimethanethiol | 2388-68-3 | 1,2-C$_6$H$_4$(CH$_2$SH)$_2$ |

According to preferred embodiment, the thiocarbamate-silane is obtained from the reaction between 3-(triethoxysilyl)propyl isocyanate and 2-mercaptoethyl sulphide, using dibutyltin dilaurate as a catalyst. The thiocarbamate synthesized by this reaction has the molecular structure:

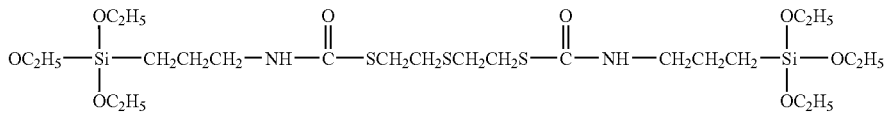

Suitable solvents are polar solvent and preferably selected from 1-methoxy-2-propanol, 4-hydroxy-4-methyl-2-pentanone, methanol, ethanol, iso-propanol, methyl-ethyl-acetone, tetrahydrofurane. A preferred solvent is 1-methoxy-2-propanol.

The coating solution preferably contains from 25 to 50 wt % thiocarbamate-silane matrix precursor which is dissolved to solvent.

The thiocarbamate-silane as described above can be combined with inorganic oxides to provide an abrasion-resistant matrix formulation. Such a formulation is consequently applied on a glass substrate and cured to form a coating layer.

In addition, the thiocarbamate-silane matrix precursor, may be used in combination with other organo-silane compounds. According to a preferred embodiment, the thiocarbamate-silane can be added to another matrix precursor such as tetraethyl orthosilicate. The performances and the refractive index of the resulting coating can be adjusted by varying the proportions of the thiocarbamate-silane to tetraethyl orthosilicate.

The abrasion-resistant coating solution of the present invention may further comprise from 0 to 20 weight percent, preferentially from 5 to 20 weight percent of a second organo-silane which is preferentially tetraethyl orthosilicate.

The abrasion-resistant coating solution comprises also from 30 to 50 weight percent, based on the total weight of the solution, of a inorganic oxide selected from the group consisting of silicon dioxide (silica), aluminum oxide (alumina), antimony oxide, tin dioxide, titanium dioxide, zirconium dioxide and mixtures of such inorganic oxides.

The inorganic oxide may be in the form of a sol. As used in the present specification, the term sol means and includes a colloidal dispersion of finely divided solid inorganic oxide particles in an aqueous or an organic liquid.

Examples of the above inorganic oxide include $SiO_2$, $Al_2O_3$, $SnO_2$, $Sb_2O_5$, $Ta_2O_5$, $CeO_2$, $La_2O_3$, $Fe_2O_3$, $ZnO$, $WO_3$, $ZrO_2$, $In_2O_3$ and $TiO_2$ alone or by mixture of at least two of them.

Said multi-component oxide(s) may be composed at adequate contents by their refractive index, and more preferably, at least one of $TiO_2$—$ZrO_2$—$SnO_2$, $TiO_2$—$ZrO_2$—$SiO_2$ and Ti—Sn—Si may be used. Preferred multi-component oxide is Optolake ESS-2® that is a $TiO_2$—$ZrO_2$—$SiO_2$ composite with core-shell structure.

Said inorganic oxide may be included in the coating composition in an amount of from 30 to 50 weight % of the solution, and more preferably from 30 to 40 weight % of the solution.

Organic solvents can be added in the abrasion-resistant solution. Suitable organic solvents are those that will dissolve or disperse the components of the coating composition. For example, the amount of solvent present may range from 20 to 90 weight % based on the total weight of the coating solution and depends, in part, on the amount of organo-silane present in the coating composition.

Hydrolysis reaction of the thiocarbamate-silane matrix precursor and eventually the other organo-silanes can use an acid catalyst.

The coating solution preferably contains a catalyst, advantageously an acid catalyst that may be selected from the group consisting of acetic acid, phosphoric acid, sulfuric acid, chloric acid, nitric acid, chlorosulfonic acid, p-toluene sulfonic acid, trichloro acetic acid, polyphosphoric acid, iodic acid, iodic anhydride, and perchloric acid.

Said acid catalysts may be used alone or in combination with two or more of said compounds, considering the final pH of the coating composition, reaction speed classified by the ingredients of the coating solution, and adhesion property for applying to a substrate.

The abrasion-resistant coating solution may be prepared according to a following process. The sol-gel reaction may be conducted at a temperature of from 20 to 35° C. by adding the inorganic oxides under stirring conditions, and subsequently adding the catalyst and eventually other additives.

The abrasion-resistant coating solution may also include an effective amount of at least one thermal curing catalyst. These thermal curing catalysts are preferably titanium complexes, preferably chosen from Tyzor LA® (Lactic acid Titanium chelate, from Dupont) and Tyzor AA-75® (Titanium acetylacetonate, from Dupont).

The amount of thermal curing catalyst used in the solution can range from 0.01 to 5% by weight based on the total composition weight, and preferentially from 0.1% to 1.0% by weight.

It may be desirable to add to the coating solution a surface active agent. The surface active agent may be non-ionic or ionic. Suitable non-ionic surfactants include compounds from fluorochemicals such as FC-4430 manufactured by 3M Company, fluorinated alkylalkoxylates, fluorinated alkyl sulfoamides, fluorinated alkyl esters, monoglyceryl series, the sorbitan fatty acid ester, the cane sugar esters, the polyoxyethylene ethers of higher fatty acids, the polyoxyethylene esters of higher fatty acids, the polyoxyethylene ethers of sorbitan esters, the fatty acid alkanolamides, polyoxyethylenes and polyoxypropylenes. Concentration of the surfactant should be greater than 0.01% by weight and preferably between 0.01 and 5% by weight, based on the total weight of the solution.

The solution may also contain a leveling agent, a lubricity providing agent, ultraviolet light absorber, antioxidant, antistatic agent, bluing agent and the like as required. The leveling agent and the lubricity providing agent are particularly preferably a copolymer of a polyoxyalkylene and polydimethylsiloxane or a copolymer of a polyoxyalkylene and fluorocarbon. They may be contained in the solution in an amount of 0.001 to 10 wt %.

Typically, after curing, the coating advantageously comprises:
25 to 50 wt % of matrix derived from a thiocarbamate-silane as a first organo-silane compound, 30 to 50 wt % of an inorganic oxide,
0 to 20 wt % of matrix derived from a second organo-silane compound, and
0.1 to 0.5 wt % of a catalyst.

According a preferred embodiment, after curing, the abrasion-resistant coating advantageously contains:
50 wt % of matrix derived from a thiocarbamate-silane precursor as a first organo-silane compound,
30 wt % of a inorganic oxide,
20 wt % of matrix derived from a second organo-silane compound, and
0.1 to 0.5 wt % of a catalyst.

According to another embodiment the invention relates to a lens, for example an ophthalmic lens, being coated with an abrasion-resistant coating composition as described above.

The substrate of said lens may be mineral glass and also organic glass made of, for example, polycarbonate, polyamide, polyimide, polysulfone, polyurethane, copolymers of polyester and polycarbonate, polyolefine, homopolymers and copolymers of diethylene glycol bis(allylcarbonate), homopolymers and copolymers of (meth)acrylic monomers, homopolymers and copolymers of thio(meth)acrylic monomers, homopolymers and copolymers of urethane, homopolymers and copolymers of thiourethane, epoxy homopolymers and copolymers, and episulfure homopolymers and copolymers.

Preferably, the substrate is an organic material, more preferably an organic lens. According to a preferred embodiment of the invention, the substrate is an optical lens which is selected from ophthalmic lens, ocular visor, and sight optical systems. In a preferred embodiment, the substrate is an ophthalmic lens which may be an afocal, a unifocal, a bifocal, a trifocal or a progressive lens. Each ophthalmic lens may be also untinted (crystal color), tinted, or photochromic. In such case, the substrate coated with the abrasion-resistant coating may be overcoated with classical properties enhancing coatings such as anti-reflecting coating and top coat.

Process for Manufacturing an Abrasion-resistant Article

The invention also relates to a process for manufacturing an abrasion-resistant article comprising the steps of preparing an abrasion-resistant coating solution as described above, and applying said solution to a substrate.

The invention deals with a process for manufacturing a high refractive and abrasion-resistant article comprising the steps of
1) preparing a coating solution by mixing
   a first organo-silane chosen from thiocarbamate-silane matrix precursor containing at least one terminal alkoxysilane group, or hydrolysates thereof, said thiocarbamate-silane compound resulting from the reaction of a polythiol comprising at least two —SH thiol substituent, with an isocyanato-silane compound represented by the general formula:

$(R_1)_3Si-R_2-N=C=O$ wherein $R_1$ represents a group selected from linear or branched ($C_1$-$C_6$) alkoxy, and $R_2$ represents a group selected from linear or branched ($C_1$-$C_6$) alkylene, linear or branched ($C_1$-$C_6$) alkenylene, arylene, and ($C_5$-$C_{12}$)cycloakylene, each of these groups being optionally substituted by one to six groups selected from halogen, alkoxy, carboxy, alkylcarbonyl, alkoxycarbonyl, and perfluoroalkyl,
   an inorganic oxide selected from the group consisting of iron, titanium, cerium, zirconium, antimony, zinc, tin oxides, silica, and composite oxides thereof,
   a curing catalyst for said organo-silane, and
   a solvent for said organo-silane,
2) coating a substrate with said solution, and
3) curing the coating, thereby obtaining a high refractive and abrasion-resistant layer coated onto said substrate.

According to particular embodiment, the process of the invention includes the steps of:
treating the surface of the substrate with chemical solutions, corona treatment, and/or thermal treatment, each of these treatment being followed by a rinsing step;
preparing an abrasion-resistant composition,
and coating said abrasion-resistant composition onto the resulting treated surface.

According to the invention the coating step of the manufacturing process may be obtained by a method selected from spin, dip, flow, fan-coater or spray, and particularly spin-coating and dip-coating steps, are easy to perform, and therefore the process.

The abrasion-resistant composition may be applied either to the convex or to the concave side of the lens, or on the two sides.

The hard coat film should preferably have a dry thickness of from 0.2 to 10 micron and should be preferably controlled to have a refractive index of from 1.48 to 1.70, although depending on the type of substrate and the purpose in end use.

According one embodiment, the lens is first coated with a primer and then cured, before being coated with the abrasion-resistant coating formulation. Such primer may include a primer latex layer comprising urethane function, or comprising (meth)acrylic function or comprising butadiene units. Suitable latex layer is preferably made of the composition described respectively in the following patents: U.S. Pat. Nos. 5,316,791, 6,503,631 and 6,489,028, incorporated herewith by reference. It is also possible to use as primer latex a photochromic latex as described in EP 1 161 512 and FR 2 811 322. More preferably, the primer latex layer used in the present invention is an aqueous dispersion of polyurethane and particularly preferred commercially available aqueous polyurethane dispersions include W-240 and W-234 (Baxenden®).

The invention also concerns thiocarbamate-silane matrix precursor obtained by reacting:
an isocyanato-silane compound represented by the general formula (I):

$(R_1)_3Si-R_2-N=C=O$ (1)

wherein $R_1$ represents a group selected from linear or branched ($C_1$-$C_6$) alkoxy, and $R_2$ represents a group selected from linear or branched ($C_1$-$C_6$) alkylene, linear or branched ($C_1$-$C_6$) alkenylene, arylene, and ($C_5$-$C_{12}$)cycloakylene,
each of these groups being optionally substituted by one to six groups selected from halogen, alkoxy, carboxy, alkylcarbonyl, alkoxycarbonyl, and perfluoroalkyl;
and a polythiol compound comprising at least two —SH thiol.

Preferentially, the invention concerns thiocarbamate-silane matrix precursor obtained by reacting:
isocyanato-silane compound represented by the general formula (I), wherein $R_1$ is selected from methoxy, ethoxy, and propyloxy, and $R_2$ is selected from linear or branched ($C_1$-$C_6$) alkylene, phenylene and cyclopropylene.

More particularly, the thiocarbamate-silane matrix precursor is obtained by reacting 3-(triethoxysilyle)propyl isocyanate and 2-mercaptoethyl sulphide.

The following examples refer to particular embodiments of the invention and shall not be interpreted as limiting the scope of this invention.

EXAMPLE 1

Synthesis of Thiocarbamate-silane Matrix Precursor

This example describes the reaction between 3-(triethoxysilyle)propyl isocyanate and a polythiol. The polythiol can be:
2-mercaptoethyl sulphide (polythiol compound I)
trimethylopropane tris(3-mercaptopropionate) (polythiol compound II)
pentaerythritol tetrakis (3-mercaptopropionate) (polythiol compound III) or
4-mercaptomethyl-3,6-dithia-1,8-octanedithiol (polythiol compound IV)

The thiocarbamate-silane is prepared by mixing the polythiol compound with 3-(triethoxysilyle)propyl isocyanate using dibutyltin dilaurate as a catalyst. The thiocarbamate-silane I obtained with polythiol compound I has the molecular structure:

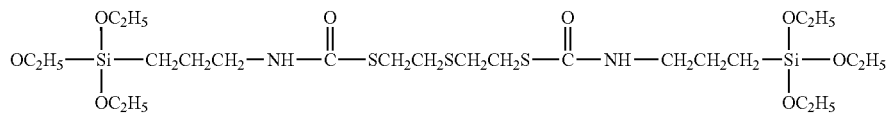

A solution of 0.2 mol of (3-isocyanatopropyl)triethoxysilane (IPTEOS) dissolved in 16 ml of anhydrous THF was added dropwise to a solution of 0.1 mol of 2-mercaptoethyl sulphide and several drops of dibutyltin dilaurate as catalyst in 100 ml of THF, at 60° C. under nitrogen. After stirring for several hours, the product is obtained by distillation of THF and followed by purification using vacuum distillation.

The thiocarbamate-silane II, III and IV are obtained using the same process as described hereinbefore by using respectively polyol compound II, III and IV.

|  | Thiocarbamate-silane I | Thiocarbamate-silane II | Thiocarbamate-silane III | Thiocarbamate-silane IV |
| --- | --- | --- | --- | --- |
| Refractive index | 1.49 | 1.5 | 1.48 | 1.48 |

EXAMPLE 2

Abrasion-resistant Coated Lens

Four coating solutions containing as a thiocarbamate-silane matrix precursor one of the compounds synthesized in example 1, are prepared according to the following process:

| Coating Solution: ingredients | Proportions [wt %] |
| --- | --- |
| 1-Methoxy-2-Propanol (solvent) | 30 |
| Optolake ESS-2 ® | 30 |
| Thiocarbamate-silane of example 1 | 20 |
| Tetraethylorthosilane | 19.9 |
| Catalyst | 0.1 |

Experiment Steps:
Dissolve thiocarbamate-silane (I, II, III or IV) synthesised in example 1, and the tetraethylorthosilane in the solvent by stirring the mixture for 1 hour;
Add HCl (0.001N) drop-wise and allow 1 hour for hydrolysis;
Add inorganic oxide composite and stir for 24 hours to achieve complete hydrolysis and mixing;
Add catalyst and surfactant and stir for 24 hours;
Store the formulation at 4° C.

Spin-coat the formulation onto lens MR-8 (made by Chemiglass Co., refractive index 1.59), cure it at 75° C. for 15 minutes and finally post-cure it at 105° C. for 3 hours.

Performance Tests of abrasion-resistant coated MR-8 Lenses are given in Table 2.

TABLE 2

| Performance Tests of abrasion-resistant coated MR-8 Lenses | Coating Solution with Thiocarbamate-silane I | Coating with Thiocarbamate-silane II | Coating Solution with Thiocarbamate-silane III | Coating Solution with Thiocarbamate-silane IV |
| --- | --- | --- | --- | --- |
| Refractive index | 1.62 | 1.63 | 1.60 | 1.59 |
| Transmission [%] |  |  |  | >89 |
| Haze | 0.1 | 0.1 | 0.2 | 0.3 |
| ASTM Bayer | 1.0 | 1.4 | 1.2 | 1.3 |

ASTM Bayer Abrasion Resistant Measurement

Bayer abrasion resistance is determined by measuring the percent haze of a coated and uncoated lens, before and after testing on an oscillating sand abrader as in ASTM F 735-81. The abrader is oscillated for 300 cycles with approximately 500 g of aluminum oxide ($Al_2O_3$) ZF 152412 supplied by Specially Ceramic Grains. The haze is measured using a Pacific Scientific Hazemeter model XL-211. The ratio of the uncoated lens haze (final-initial) is a measure of the performance of the coating, with a higher ratio meaning a higher abrasion resistance.

EXAMPLE 3

Abrasion-resistant Coated Lens

The following coating solution is prepared following the steps described in example 2.

| Component | name | wt % in coating solution | wt % in cured coating |
| --- | --- | --- | --- |
| Solvent | 1-Methoxy-2-Propanol | 34% |  |
| Thiocarbamate-silane I of example 1 | $S[CH_2CH_2SCONH(CH_2)_3Si(OCH_2CH_3)_3]_2$ | 17% | 47% |
| Other organo-silane | Tetraethyl orthosilicate | 17% | 20% |
| Metal oxide | Optolake ESS-2 ® | 30.7% | 29% |

-continued

| Component | name | wt % in coating solution | wt % in cured coating |
|---|---|---|---|
| Catalyst | Titanium acetylacetonate (Tyzo AA 75 ® from DUPONT) | 1.0% | 3.6% |
| Surfactant | Ciba EFKA 3034 ® | 0.3% | 0.4% |

The solution is then spin-coated onto lens MR-8 (made by Chemiglass Co., refractive index 1.59), cure it at 75° C. for 15 minutes and finally post-cure it at 105° C. for 3 hours.

Performance Tests of abrasion-resistant coated MR-8 Lenses are given below.

| | |
|---|---|
| Haze | 0.15 |
| Transmittance | 90.5% |
| Bayer | 1.6 |

The performances and the refractive index of the resulting coating can be adjusted by varying the proportions of the thiocarbamate-silane to tetraethylorthosilicate (TEOS).

| Ingredient name | wt % in coating solution | | | | |
|---|---|---|---|---|---|
| 1-Methoxy-2-Propanol | | | 34 | | |
| Thiocarbamate-silane I of example 1 | 50.4 | 47.9 | 40.4 | 30.5 | 25.58 |
| Tetraethyl orthosilicate | — | 2.49 | 10.0 | 19.9 | 24.6 |
| Optolake ESS-2 ® | | | | 30.7 | |
| Titanium acetylacetonate (Tyzo AA 75 ® from DUPONT) | | | 1.0 | | |
| Ciba EFKA 3034 ® | | | 0.3 | | |
| Performance tests | | | | | |
| Refractive index of abrasion-resistant coated MR-8 Lenses | 1.620 | 1.604 | 1.590 | 1.583 | 1.578 |
| Bayer of abrasion-resistant coated MR-8 Lenses | 0.8 | 1.0 | 1.0 | 1.4 | 1.8 |

When incorporating a second organo-silane in the coating solution, the content must be less than 20% by weight of the weight of the solution in order not to have a Bayer value higher than 1.6.

The performances and the refractive index of the resulting coating can be adjusted by varying the proportions of the thiocarbamate-silane to Optolake ESS-2®.

| Ingredient name | wt % in coating solution | | |
|---|---|---|---|
| 1-Methoxy-2-Propanol | 18 | 22 | 26 |
| Thiocarbamate-silane I of example 1 | 20 | 26 | 33 |
| Optolake ESS-2 ® | 61 | 51 | 40 |
| Titanium acetylacetonate (Tyzo AA 75 ® from DUPONT) | | 0.7 | |
| Ciba EFKA 3034 ® | | 0.3 | |

| | wt % in coating solution | | |
|---|---|---|---|
| Performance tests | | | |
| Refractive index of abrasion-resistant coated MR-8 Lenses | 1.66 | 1.64 | 1.62 |
| Haze | 0.1-0.2 | 0.1-0.2 | 0.1-0.2 |
| Bayer of abrasion-resistant coated MR-8 Lenses | 1.2 | 1.1 | 0.9 |

The invention claimed is:

1. An optical article comprising a transparent substrate, and a high refractive and abrasion-resistant layer coated onto at least one surface of said substrate, wherein said layer results from reacting and curing a mixture containing the following compounds:
a first organo-silane compound chosen from thiocarbamate-silane compounds containing at least one terminal alkoxysilane group, or hydrolysates thereof, said thiocarbamate-silane compound resulting from the reaction of a polythiol comprising at least two —SH thiol substituent, with an isocyanato-silane compound represented by the general formula:

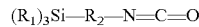

$(R_1)_3Si\text{---}R_2\text{---}N\text{=}C\text{=}O$ wherein $R_1$ represents a group selected from linear or branched ($C_1$-$C_6$) alkoxy, and $R_2$ represents a group selected from linear or branched ($C_1$-$C_6$) alkylene, linear or branched ($C_1$-$C_6$) alkenylene, arylene, and ($C_5$-$C_{12}$) cycloakylene, each of these groups being optionally substituted by one to six groups selected from halogen, alkoxy, carboxy, alkylcarbonyl, alkoxycarbonyl, and perfluoroalkyl, wherein the polythiol is selected from the group consisting of 4-mercaptomethyl-3,6-dithia-1, 8-octanedithiol, trimethylolpropane tris(3-mercapto propionate), pentaerythritol tetrakis(3 mercaptoacetate), trimethylolpropane tris(3-mercaptoacetate), 4-t-butyl-1,2 benzenedithiol, bis-(2-mercaptoethyl)sulfide, 4,4'-thiodibenzenethiol, benzenedithiol, glycol dimercaptoacetate, glycol dimercaptopropionate ethylenebis(3 mercaptopropionate), polyethylene glycol dimercaptoacetates, polyethylene glycol di(3 mercaptopropionates), pentaerythritol tetrakis(3-mercapto-propionate), tris-(3-mercaptopropyl)isocyanurate, 1,2,3-trimercaptopropane, 2,2-bis(mercaptomethyl)-1,3-propanedithiol, dipentaerythrithiol, 1,2,4-trimercaptomethyl benzene, 2,5-dimercaptomethyl-1,4-dithiane, bisphenofluorene bis(ethoxy-3-mercaptoproprionate), 4,8-bis(mercaptomethyl)-3,6,9 trithia-1,11-undecanedithiol, 2-mercaptomethyl-2-methyl-1,3-propanedithiol, 1,8-dimercapto-3,6-dioxaoctane, thioglycerol bismercapto-acetate, and mixtures thereof,
an inorganic oxide selected from the group consisting of iron, titanium, cerium, zirconium, antimony, zinc, tin oxides, silica, and composite oxides thereof,
a curing catalyst for said organo-silane, and
a solvent for said organo-silane.

2. Optical article according to claim 1, wherein the coating solution comprises from 30% to 50% by weight of the inorganic oxide, based on the total weight of the solution.

3. Optical article according to claim 1, wherein the coating solution comprises from 25% to 50% by weight of the first organo-silane, based on the total weight of the solution.

4. Optical article according claim 1, wherein first organo-silane compound has a refractive index higher than 1.55.

5. Optical article according to claim 1, wherein the isocyanato-silane compound comprises a $R_1$ group selected from methoxy, ethoxy, and propyloxy, and $R_2$ group selected from linear or branched ($C_1$-$C_6$) alkylene, phenylene and cyclopropylene.

6. Optical article according claim 1, wherein the polythiol is selected from the group consisting of 2-mercaptoethyl sulphide, trimethylopropane tris(3-mercaptopropionate), pentaerythritol tetrakis (3-mercaptopropionate) and 4-mercaptomethyl-3,6-dithia-1,8-octanedithiol.

7. Optical article according to claim 1, wherein the isocyanato-silane is selected from the group consisting of 1-trimethoxysilane-4-isocyanato-benzene, 1-trimethoxysi lane-3-isocyanato-benzene, 1-trimethoxys lane-2-isocyanato-cyclopropane, 1-trimethoxysilane-3-isoeyanato-propane, and 3-(triethoxysilyl)propyl isocyanate.

8. Optical article according to claim 1, wherein the inorganic oxide is selected from $SiO_2$, $Al_2O_3$, $SnO_2$, $Sb_2O_5$, $Ta_2O_5$, $CeO_2$, $La_2O_3$, $Fe_2O_3$, ZnO, $WO_3$, $ZrO_2$, $In_2O_3$ and $TiO_2$ alone or by mixture of at least two of them.

9. Optical article according to claim 1, wherein the inorganic oxide is a $TiO_2$—$ZrO_2$—$SiO_2$ composite.

10. Optical article according to claim 1, wherein the solvent is chosen from 1-methoxy-2-propanol, 4-hydroxy-4-methyl-2-pentanone, methanol, ethanol, iso-propanol, methyl-ethyl-cetone, and tetrahydrofurane.

11. Optical article according to claim 1, wherein said reaction mixture further includes a second organo-silane, preferentially tetraethyl orthosilicate.

12. Optical article according to claim 1, wherein said substrate is selected from the group consisting of sight optical systems, ocular visors, and ophthalmic lenses, said ocular visors and ophthalmic lenses optionally being untinted, tinted or photochromic.

13. Process for manufacturing an optical article according to claim 1, comprising the steps of:
1) preparing a coating solution by mixing
a first organo-silane chosen from thiocarbamate-silane compounds containing at least one terminal alkoxysilane group, or hydrolysates thereof, said thiocarbamate-silane compound resulting from the reaction of a polythiol comprising at least two —SH thiol substituent, with an isocyanato-silane compound represented by the general formula:

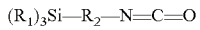

wherein $R_1$ represents a group selected from linear or branched ($C_1$-$C_6$) alkoxy, and $R_2$ represents a group selected from linear or branched ($C_1$-$C_6$) alkylene, linear or branched ($C_1$-$C_6$) alkenylene, arylene, and ($C_5$-$C_{12}$) cycloakylene, each of these groups being optionally substituted by one to six groups selected from halogen, alkoxy, carboxy, alkylcarbonyl, alkoxycarbonyl, and perfluoroalkyl, wherein the polythiol is selected from the group consisting of 4-mercaptomethyl-3,6-dithia-1,8-octanedithiol, trimethylolpropane tris(3-mercaptopropionate), pentaerythritol tetrakis(3 mercaptoacetate), trimethylolpropane tris(3-mercaptoacetate), 4-t-butyl-1,2 benzenedithiol, bis-(2-mercaptoethyl)sulfide, 4,4'-thiodibenzenethiol, benzenedithiol, glycol dimercaptoacetate, glycol dimercaptopropionate ethylenebis(3 mercaptopropionate), polyethylene glycol dimercaptoacetates, polyethylene glycol di(3 mercaptopropionates), pentaerythritol tetrakis(3-mercapto-propionate), tris-(3-mercaptopropyl)isocyanurate, 1,2,3-trimercaptopropane, 2,2-bis(mercaptomethyl)-1,3-propanedithiol, dipentaerythrithiol, 1,2,4-trimercaptomethyl benzene, 2,5-dimercaptomethyl-1,4-dithiane, bisphenofluorene bis(ethoxy-3-mercaptoproprionate), 4,8-bis(mercaptomethyl)-3,6,9 trithia-1,11-undecanedithiol, 2-mercaptomethyl-2-methyl-1,3-propanedithiol, 1,8-dimercapto-3,6-dioxaoctane, thioglycerol bismercapto-acetate, and mixtures thereof,
an inorganic oxide selected from the group consisting of iron, titanium, cerium, zirconium, antimony, zinc, tin oxides, silica, and composite oxides thereof,
a curing catalyst for said organo-silane, and
a solvent for said organo-silane,
2) coating a substrate with said solution, and
3) curing the coating, thereby obtaining a high refractive and abrasion-resistant layer coated onto said substrate.

14. Process according to claim 13, wherein the coating solution further contains a second organo-silane representing from 5% to 20% by weight of the total weight of the solution.

15. Process according to claim 13, wherein after curing step 3), the coating comprises:
25 to 50 wt % of matrix derived from a thiocarbamate-silane as a first organo-silane compound,
30 to 50 wt % of an inorganic oxide,
0 to 20 wt % of matrix derived from a second organo-silane compound, and
0.1 to 0.5 wt % of a catalyst.

16. Process according to claim 13, wherein after curing step 3), the coating comprises:
50 wt % of matrix derived from a thiocarbamate-silane precursor as a first organo-silane compound,
30 wt % of a inorganic oxide,
20 wt % of matrix derived from a second organo-silane compound, and
0.1 to 0.5 wt % of a catalyst.

17. An ophthalmic lens comprising an optical article according to claim 1 wherein the ophthalmic lens is an afocal, unifocal, bifocal, trifocal, or progressive lens.

* * * * *